United States Patent

Kirsch

Patent Number: 5,824,088
Date of Patent: Oct. 20, 1998

[54] COVER DEVICE FOR BONE VOIDS AND METHOD FOR THE MANUFACTURE THEREOF

[76] Inventor: Axel Kirsch, Talstr. 23, 70772 Filderstadt, Germany

[21] Appl. No.: 732,224

[22] PCT Filed: Feb. 13, 1995

[86] PCT No.: PCT/EP95/00519

§ 371 Date: Dec. 17, 1996

§ 102(e) Date: Dec. 17, 1996

[87] PCT Pub. No.: WO95/28900

PCT Pub. Date: Nov. 2, 1995

[30] Foreign Application Priority Data

Apr. 27, 1994 [DE] Germany .......................... 44 14 675.2

[51] Int. Cl.⁶ .................................................... A61F 2/28
[52] U.S. Cl. ................................ 623/16; 623/11; 606/70; 606/76
[58] Field of Search ......................... 623/16, 11; 606/69, 606/70, 71, 72, 74, 76, 77

[56] References Cited

U.S. PATENT DOCUMENTS

| | | | |
|---|---|---|---|
| 4,338,926 | 7/1982 | Kummer et al. | 623/16 |
| 4,403,606 | 9/1983 | Woo et al. | 623/16 |
| 4,693,721 | 9/1987 | Ducheyne | 623/16 |
| 4,955,911 | 9/1990 | Frey et al. | |
| 5,002,583 | 3/1991 | Pitaru et al. | 623/16 |
| 5,019,096 | 5/1991 | Fox, Jr. et al. | 623/16 |
| 5,061,286 | 10/1991 | Lyle | 623/16 |
| 5,211,661 | 5/1993 | Shinjou et al. | 623/16 |
| 5,380,328 | 1/1995 | Morgan | 623/16 |
| 5,397,359 | 3/1995 | Mittelmeier et al. | |
| 5,443,483 | 8/1995 | Kirsch | 623/16 |
| 5,466,262 | 11/1995 | Saffran | 606/74 |

FOREIGN PATENT DOCUMENTS

| | | |
|---|---|---|
| 0 338 976 | 10/1989 | European Pat. Off. . |
| 0 504 103 | 9/1992 | European Pat. Off. . |
| 0 523 372 | 1/1993 | European Pat. Off. . |
| 0 525 210 | 2/1993 | European Pat. Off. . |
| 0 526 682 | 2/1993 | European Pat. Off. . |
| 9115341 U | 4/1992 | Germany . |
| 43 02 708 | 8/1994 | Germany . |
| 1 549 328 | 7/1979 | United Kingdom . |
| WO86/03667 | 7/1986 | WIPO . |
| WO88/03417 | 5/1988 | WIPO . |
| WO92/10218 | 6/1992 | WIPO . |
| WO94/03121 | 2/1994 | WIPO . |

*Primary Examiner*—Michael J. Milano
*Assistant Examiner*—Tram A. Nguyen
*Attorney, Agent, or Firm*—Hill & Simpson

[57] ABSTRACT

Cover device for temporarily covering bone voids, particularly a recess, which are filled with ossiferous material such as hydroxyl apatite granules, in the proper bone tissue of the body, comprises a perforated reinforcement element for covering the void in essentially a shape-stable fashion that is composed of relatively stiff but flexible material such as a supporting grid of metal or the like, and a single-layer or multi-layer cover membrane carried by the reinforcement element, and at least one of the layers of the cover membrane is applied as a solution film onto the reinforcing element after the use-specific shaping of the element as well as a method for the production of the element.

11 Claims, 2 Drawing Sheets

COVER DEVICE FOR BONE VOIDS AND METHOD FOR THE MANUFACTURE THEREOF

BACKGROUND OF THE INVENTION

The invention is directed to a cover device for temporarily covering bone voids, particularly a recess, filled with ossiferous material such as hydroxyl apatite granules, in the proper bone tissue of the body. The device comprises a perforated reinforcement element for covering the void in essentially shape-stable fashion that is composed of relatively stiff but flexible material such as a supporting grid of metal or the like, and a single-layer or multi-layer cover membrane carried by the reinforcement element.

A further subject matter of the invention is a method for manufacturing a cover device for temporarily covering bone voids, particularly a recess, filled with ossiferous material such as hydroxyl apatite granules, in the proper bone tissue of the body, whereby a perforated reinforcement element for covering the void in essentially shape-stable fashion is composed of relatively stiff but flexible material such as a supporting grid of metal or the like, is provided with a single-layer or multi-layer cover membrane and is brought into a use-specific shape.

It is standard in osteosurgery, for example in the reconstruction of bones in plastic surgery or in surgical operations of the jaw, to fill bone voids in the form of recesses or cavities in the proper bone tissue of the body with ossiferous material that is usually composed of a mixture of bone replacement material such as hydroxyl apatite granules and proper bone particles of the body. In order to assure that the ossiferous material is grown through with bone proceeding essentially only from the bone side but not by epithelium and sub-epithelial connective tissue in an undesirable way, the recess is closed with a cover membrane of the species initially cited. The bone void can be essentially completely eliminated, namely, only when it is assured that the ossiferous material is grown completely through in ossiferous fashion.

Up to now, polytetrafluorethylene films, for example, that must be removed after the healing of the bone void, have been employed as cover membranes. Films of resorbable material are also known.

As a consequence of the flexible plastic material employed for cover membranes, the membrane is not stiff but can change in position due to a mechanical stressing by the surrounding, soft body tissue, for example as a result of muscle movements or externally acting forces. Such micromovements of the cover membrane, which can ensue in all spatial directions, have the disadvantage that the ossiferously predetermined granulation tissue situated under the cover membrane in the direct proximity thereof that replaces the primarily arising blood coagulate under the membrane and between the particles of the ossiferous material is dedifferentiated in such a way that sub-epithelial, fibrous connective tissue develops.

DE 91 15 341 U1 discloses a supporting lattice for the acceptance of particulate bone replacement agents that is composed of a biodegradable and thermoplastically shapable polymer. The supporting lattice serve the purpose of enabling a mechanical support of bone replacement material and, for example given complete partition of the lower jaw, fixing the two resection stumps to one another. A closing of a bone recess from the non-bone tissue upon simultaneous mechanical immobilization and stabilization both relative to the surrounding, soft body tissue as well as relative to the ossiferous material is not possible with this supporting lattice.

EP 0 504 103 A1 discloses a fastening means for a cover membrane composed of tissue-compatible film; however, the problems already initially described arise given such a movable cover membrane.

The subject matter of U.S. Pat. No. 5,591,234, which claims priority from German patent application P 43 02 709.1-35 is directed to a cover device of the species with which the undisturbed conversion of the ossiferously predetermined granulation tissue forming in the bone void into bone tissue is guaranteed in that movements on the part of the cover membrane are prevented by the reinforcing element. The reinforcing element that is shaped to match, for example, the curvature of the jaw bone in which the bone void is located sees to it that the blood coagulate is converted undisturbed into bone tissue.

Given the cover device of the species, the cover membrane is connected to the reinforcement element before the use-specific shaping of the latter. This preferably ensues in that that supporting lattice is already provided with a cover membrane at the factory.

The above-described cover device of the earlier disclosure has definitely proven itself in practice; however, problems can arise, especially when an especially pronounced bending or the like of the reinforcement element is required in use-specific fashion because the previously applied cover membrane can then be easily damaged since it is not adequately elastic insofar as it has the thickness required by the specific use.

SUMMARY OF THE INVENTION

The invention is therefore based on the object of improving the cover device of the species initially cited and the method for the manufacture thereof to the effect that a faultless adaptation of the cover device to the shape of the bone void and of the proper bone of the body surrounding the void is assured even under unfavorable conditions without the risk of damaging the cover membrane.

In a development of the cover device of the species, this object is inventively achieved in that at least one of the layers of the cover membrane is applied onto the reinforcing element as a solution film after the use-specific shaping thereof.

It can thereby be provided that that surface of the reinforcing element facing toward and/or away from the bone void is provided with a biaxially stretchable base film of the cover membrane.

The invention also proposes that the solution film is applied onto the base film and/or films of the cover membrane.

It can also be provided in the invention that hydroxyl apatite particles or the like are embedded into the solution film.

A further embodiment of the invention provides that the solution film of the cover membrane comprises at least one film-forming material from the group containing cyanoacrylate, collagen, polytetrafluorethylene, polycarbonate, polyurethane, polyactid/vicryl, polyactid, oxymethyl cellulose and methylmethacrylate.

In a development of the method of the species, the inventive method is characterized in that at least one of the layers of the cover membrane is not applied as the solution film onto the reinforcing element until after the use-specific shaping of the latter.

It can thereby be provided that a biaxially stretchable base film of the cover membrane is applied onto that side of reinforcing element facing toward and/or away from the bone void before the application of the solution film.

The invention further provides that the solution film is placed onto the reinforcing element upon interposition of (one of) the base film(s).

It is thereby inventively provided that the reinforcing element or, respectively, the surface of the base film or films intended for the acceptance of the solution film is occupied with hydroxyl apatite powder or the like before the application of the solution film.

It can thereby be provided for manufacturing the solution film that a solution of a solution film-forming material, which comprises at least one constituent from the group containing cyanoacrylate, collagen, polytetrafluorethylene, polycarbonate, polyurethane, polyactid/vicryl, polyactid, oxymethyl cellulose and methylmethacrylate, is applied in an organic solvent onto the reinforcing element or, respectively, the base foil/one of the base foils of the cover membrane.

The invention also proposes that the solution is sprayed onto the reinforcing element or, respectively, the surface of the base foil or foils intended for the acceptance of the solution film.

It is thereby inventively provided that the solution is applied onto the reinforcing element or, respectively, the surface of the base film or films intended for the acceptance of the solvent by painting, brushing or the like.

In particular, it can thereby also be inventively provided that the application of the solvent film ensues in situ after the application of the reinforcing element to the bone void.

The invention is based on the surprising perception that any difficulties, which may exist in specific applications or employment of the cover device of the species can be successfully eliminated if the reinforcing element, which may be a supporting lattice of titanium or the like, is first lent the use-specific shaped that is needed before the cover membrane or, respectively, at least one of the layers, which is preferably the upper layer of the cover membrane, is then applied. The application of the cover membrane then ensues in the fashion of a spray-on bandage by forming a solution film, whereby a polymerization process can also be included as warranted.

Given application of the invention, one can shape the reinforcing element to the ultimate shape before application to the bone void, for example upon employment of a model or of a template, and then the cover membrane is applied by being formed from and a solution films, however, one can also proceed in an especially beneficial way by applying of the reinforcing element to the bone void to first have the ultimate shaping before the cover membrane or, respectively, at least one layer thereof is applied as the solution film like a spray-on bandage.

It is thereby especially beneficial that, as provided in an embodiment of the invention, hydroxyl apatite powder or the like can be embedded in the solution film, the growing process being especially promoted as a result thereof. Of course, it is also possible to employ a reinforcing element that has already been provided with a thin base film of the cover membrane on or both sides before the solution film is sprayed on the base film. The same materials are suitable for this base film as well as for the solution film of the cover membrane of which the former, or course, can also be entirely composed.

Further features and advantages of the invention derive from the claims and from the following description in which exemplary embodiments are explained in detail on the basis of the schematic drawing.

DESCRIPTION OF THE PREFERRED EMBODIMENTS

Figure 1:
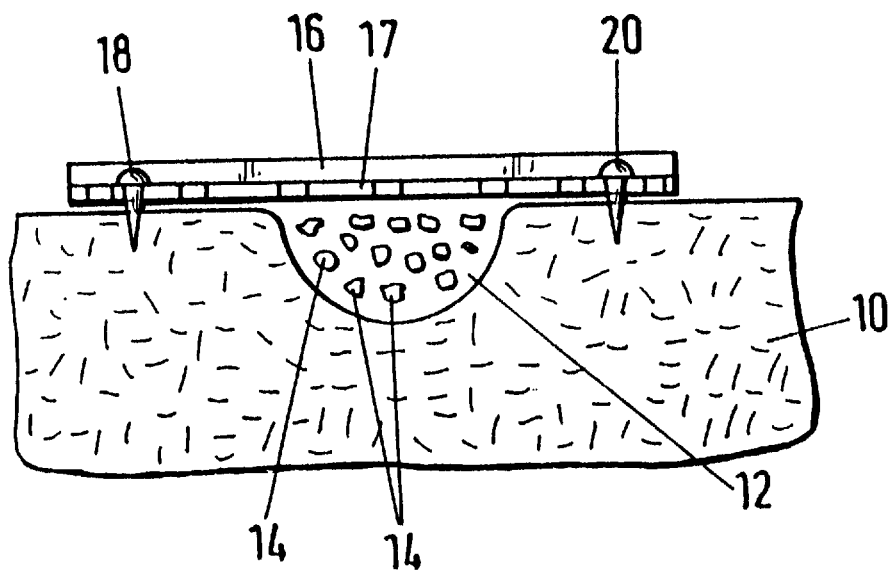
FIG. 1 is a cross sectional view of a bone void covered with a cover device according to an exemplary embodiment of the invention.

As FIG. 1 shows, a bone void formed by a recess 12 in as proper bone 10 of the body is essentially completely filled with ossiferous material 14 of hydroxyl apatite granules, whereby bone particles composed of proper bone tissue of the body are added in a known way to these hydroxyl apatite granules. The recess 12 filled with the ossiferous material 14 is covered by a cover membrane 16 that is arranged at that side of a reinforcing element composed of a perforated, thin titanium plate that faces away from the bone 10. The cover membrane 16 and the reinforcing element 17 are secured tightly seated against the proper bone 10 of the body with fastening nails 18, 20 at all sides of the recess 12. The cover membrane 16 has the purpose of assuring that the proper bone 10 of the body grows through the ossiferous material in an ossiferous way such that tissue other than bone tissue, particularly mucous membrane tissue, is prevented from permeating the ossiferous material.

In the exemplary embodiment of FIG. 1, the cover membrane 16 is fashioned as a single-layer solution film of breathable methylmethacrylate that has been applied onto the reinforcing element 17 after the ultimate shaping thereof.

Figure 2:
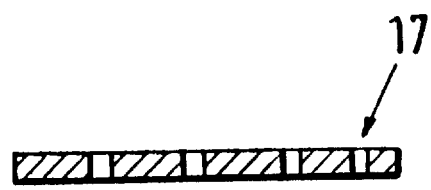
FIG. 2 is an enlarged cross sectional view of reinforcing element of the cover device of FIG. 1.

In an enlarged view, FIG. 2 shows the reinforcing element 17 composed of perforated titanium sheet that is employed in the exemplary embodiment of FIG. 1 and on which the cover membrane 16 has been applied as a solution film.

Figure 3:
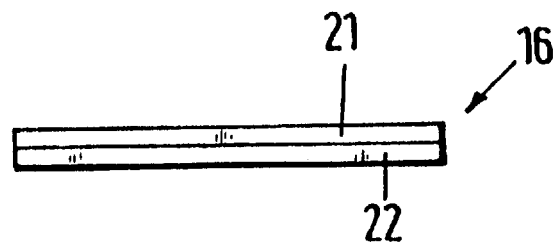
FIG. 3 is an enlarged cross sectional view of a further exemplary embodiment of the cover membrane of the cover device of FIG. 1.

In the exemplary embodiment of FIG. 3, the cover membrane 16 is composed of a base film 22 of oxymethyl cellulose that is so thin that it can be easily biaxially shaped, whereby, thus, the base foil 22 is first applied onto the reinforcing element 17 before the shaping thereof. When the reinforcing element 17 is shaped, the base film 22 is correspondingly biaxially stretched without tearing. A solution film 21 is then applied onto the ultimately shaped reinforcing element.

Figure 4:
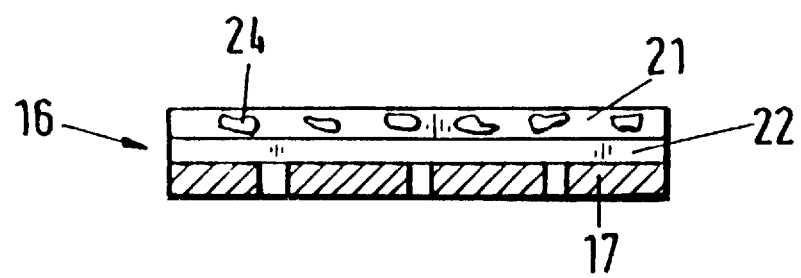
FIG. 4 is an enlarged cross sectional view of a third exemplary embodiment of the cover device of the invention

In the exemplary embodiment of FIG. 4, the reinforcing element 17 initially carries the base film 22 already present in the exemplary embodiment of FIG. 3. The solution film 21 in which hydroxyl apatite particles 24 are embedded is then applied on the base film 22.

Figure 5:
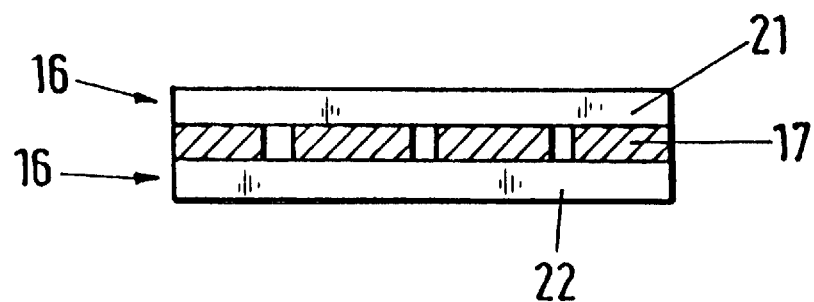
FIG. 5 is an enlarged cross sectional view a fourth exemplary embodiment of a cover device of the invention

In the exemplary embodiment of FIG. 5, the base film 22 is located at that side of the reinforcing element facing toward the bone and lying at the bottom in the drawing, whereas the solution film 21 is located at that side of the reinforcing element 17 facing away from the bone (not shown in FIG. 5). The manufacture of the cover device according to FIG. 1 ensues in such a way that, following the ultimate shaping of the reinforcing element 17, a methacrylic acid methyl ester solution is sprayed onto it like the production of a spray-on bandage. The solution film 16 then is formed after the organic solvent evaporates.

In the exemplary embodiment of FIG. 3, one proceeds in such a way that the solution of the solvent-forming material is sprayed onto the base film 22.

In the exemplary embodiment of FIG. 4, one proceeds such that that surface of the base film 22 facing away from the reinforcing element 17 is first dusted with hydroxyl apatite powder. Subsequently, the solution film 21 is then applied, again by spraying, the hydroxyl apatite particles 24 being then embedded in the solution film 21 as a result thereof.

In the exemplary embodiment of FIG. 5, the procedure is such that the solution of the solvent-forming material is painted onto the reinforcing element 17 at the side facing away from the base film 22, whereby the solution film 21 is then formed by evaporation of the organic solvent.

Both individually as well as in arbitrary combination, the features of the invention disclosed in the above description, in the drawings as well as in the claims can be critical for the realization of the various embodiments of the invention.

I claim:

1. In a method for producing a cover device for temporarily covering a bone void including a recess in a proper bone tissue of a body, which void is filled with an ossiferous material including hydroxyl apatite granules, said method including providing a perforated reinforcing element for covering the void in an essentially shape-stable fashion, which element is composed of a relatively stiff but flexible material in the form of a supporting grid of metal, and is provided with a cover membrane of at least one layer, and shaping the reinforcing element into the use-specific shape to produce the cover device, the improvements comprising providing the cover membrane by applying a biaxially stretchable base film on a surface of the reinforcing element and applying a solution film on the reinforcing element after the steps of shaping the element into the use-specific shape and applying a biaxially stretchable base film.

2. In a method according to claim 1, wherein the step of applying a solution film places the solution film on the base film.

3. In a method according to claim 1, which includes embedding a hydroxyl apatite powder in the solution film by applying the powder on a surface before the step of applying the solution film.

4. In a method according to claim 1, wherein the step of applying the solution film includes forming a solution by mixing at least one constituent selected from a group consisting of cyanoacrylate, collagen, polytetrafluorethylene, polycarbonate, polyurethane, polyactid/vicryl, polyactid, oxymethyl cellulose and methylmethacrylate in an organic solvent.

5. In a method according to claim 4, wherein the step of applying the solution film comprises spraying the solution on the surface of the element.

6. In a method according to claim 4, wherein the step of applying the solution film comprises brushing the solution onto the element.

7. In a method according to claim 1, wherein the step of applying the solution film occurs in situ after placing of the reinforcing element to cover the bone void.

8. In a cover device for temporarily covering a bone void in a proper bone tissue of the body, which void is filled with ossiferous material including hydroxyl apatite granules, said cover device comprising a perforated reinforcement element for covering the void in an essentially shape-stable fashion that is composed of a relatively stiff but flexible material being shaped to a surface of the bone tissue having the void, and a cover membrane carried by the reinforcement element, the improvement comprising the cover membrane including a stretchable base film on a surface of the reinforcement element and at least one layer being applied as a solution film directly onto the base film subsequent to shaping of the element to engage the surface of the bone tissue so that the base film is between the solution film and the reinforcement element.

9. In a cover device according to claim 8, wherein the solution film of the cover membrane comprises at least one film-forming material selected from the group consisting of cyanoacrylate, collagen, polytetrafluorethylene, polycarbonate, polyurethane, polyactid/vicryl, polyactid, oxymethyl cellulose and methylmethacrylate.

10. In a cover device according to claim 8, wherein hydroxyl apatite particles are embedded into the solution film of the cover membrane.

11. In a cover device according to claim 8, wherein the base film is on the surface of the element facing away from the bone void.

* * * * *